US006107262A

United States Patent [19]
Noble, II

[11] Patent Number: 6,107,262
[45] Date of Patent: Aug. 22, 2000

[54] ENHANCED LIGHT TRANSMISSION TRANSPARENT BAR AND METHOD OF MANUFACTURE THEREOF

[76] Inventor: David S. Noble, II, 3891 N. Ventura Ave. Unit A-3, Ventura, Calif. 93001

[21] Appl. No.: 08/899,498

[22] Filed: Jul. 19, 1997

Related U.S. Application Data

[63] Continuation-in-part of application No. 08/710,190, Sep. 12, 1996.

[51] Int. Cl.[7] .............................. A61K 7/50; C11D 17/00; C11D 10/00; C11D 17/04

[52] U.S. Cl. .......................... 510/147; 510/140; 510/440; 510/455; 510/483

[58] Field of Search ..................................... 510/147, 140, 510/152, 148, 439, 440, 447, 455, 483; 206/77.1, 524.1; 220/377

[56] References Cited

U.S. PATENT DOCUMENTS

| | | | |
|---|---|---|---|
| Re. 6,624 | 8/1875 | Strunz | 510/147 |
| 1,441,315 | 1/1923 | Walbridge | 510/147 |
| 1,827,549 | 10/1931 | Villain | 510/147 |
| 1,997,474 | 4/1935 | Stone | 510/143 |
| 3,149,188 | 9/1964 | Schmitt | 264/267 |
| 3,245,197 | 4/1966 | Vam Mil, Jr. et al. | 53/28 |
| 3,413,230 | 11/1968 | Dupuis | 252/92 |
| 3,773,672 | 11/1973 | Bredice | 252/92 |
| 3,926,828 | 12/1975 | O'Neil et al. | 252/117 |
| 4,504,433 | 3/1985 | Inui et al. | 264/232 |
| 4,754,874 | 7/1988 | Haney | 206/77.1 |
| 5,002,685 | 3/1991 | Chambers et al. | 252/134 |
| 5,602,088 | 2/1997 | Tokosh et al. | 510/144 |

FOREIGN PATENT DOCUMENTS

| | | |
|---|---|---|
| 0 244 084 | 11/1987 | European Pat. Off. . |
| 0 321 179 | 6/1989 | European Pat. Off. . |
| 1 149 846 | 11/1958 | Germany . |

*Primary Examiner*—Yogendra Gupta
*Assistant Examiner*—Wohn M Petruncio

[57] ABSTRACT

An improved transparently packaged bar, having increased light transmission, and a method of manufacture thereof is disclosed. The packaged bar has an increased level of light transmission which is believed to be caused by the cooling of molten soap in direct contact with the stretchable transparent wrap which is used to package the bar. The bar has an unique shape which enhances its light transmission. The bar may also contain voids which enhance the appearance of the soap bar or reduce its density, or both. The soap bar, and method of manufacture, are particularly well suited for transparent, translucent, and pearlescent soaps, or a bar which is poured with a combination thereof. Additionally, objects both solid and amorphous, and flexible or rigid, may be placed within the bar which have an enhanced level of visibility inside the packaged soap bar. If desired, hues or pigments may be dispersed through some portion of the soap bar to obtain a desired artistic appearance. Further force may be applied to the top of the poured bar, or to the film into which the molten soap is poured to effect a curved shape having a smaller radius of curvature, or to allow the use of thicker or stronger film, or both. The wrapped bar may have a perceived optical clarity index of more than 0.9 based on the Noble Perceived Optical Clarity Test, both immediately after manufacture, and, in the event high strength film is used, at least 6 months after the date of manufacture.

22 Claims, 6 Drawing Sheets

| | RAW DATA | | | | CONTROL INDEX | | | |
|---|---|---|---|---|---|---|---|---|
| SPECIAL NUMBER | CONTROL PLAIN CHART | 6 MONTH OLD SOAP CAST IN | 6 MONTH OLD SOAP CAST IN | BRAND NEW PRIOR ART | CONTROL PLAIN CHART | SOAP CAST IN REGULAR WRAP | SOAP CAST IN BARRIER WRAP | PRIOR ART WRAPPED SOAP |
| 1 | 46 | 22 | 44 | 40 | 1.00 | 0.4783 | 0.9565 | 0.8696 |
| 2 | 39 | 12 | 40 | 34 | 1.00 | 0.3077 | 1.0256 | 0.8718 |
| 3 | 40 | 20 | 37 | 37 | 1.00 | 0.5000 | 0.9250 | 0.9250 |
| 4 | 45 | 16 | 43 | 43 | 1.00 | 0.3556 | 0.9556 | 0.9556 |
| 5 | 35 | 12 | 36 | 33 | 1.00 | 0.3429 | 1.0286 | 0.9429 |
| 6 | 35 | 13 | 33 | 26 | 1.00 | 3.0714 | 0.9429 | 0.7429 |
| 7 | 49 | 19 | 47 | 36 | 1.00 | 0.3878 | 0.9592 | 0.9388 |
| 8 | 49 | 25 | 49 | 43 | 1.00 | 0.5102 | 1.0000 | 0.8776 |
| 9 | 48 | 24 | 47 | 47 | 1.00 | .05000 | 0.9792 | 0.9792 |
| 10 | 48 | 14 | 47 | 38 | 1.00 | 0.2917 | 0.9792 | 0.7917 |
| MEAN | 43.40 | 17.70 | 42.30 | 38.70 | 1.00 | 0.4045 | 0.9752 | 0.8895 |
| STANDARD DEVIATION | 5.64 | 4.97 | 5.52 | 6.50 | 0.00 | 0.0847 | 0.0343 | 0.0752 |
| STANDARD DEVIATION X | 1.78 | 1.57 | 1.75 | 2.06 | 0.00 | 0.0268 | 0.0109 | 0.0238 |

*FIG. 11*

AKP🔔 JC@EYUSRV

BQ?XRTWŌAN

CEU9VLKZR

DX&THSM

EOYWZX

FDJMZ

*FIG. 12*

ENHANCED LIGHT TRANSMISSION TRANSPARENT BAR AND METHOD OF MANUFACTURE THEREOF

INTRODUCTION

This application is a continuation-in-part of my co-pending application Ser. No. 08/710190, filed Sep. 12, 1996. This invention relates generally to transparent bars, and more particularly to a novel transparently wrapped soap, air freshener, or the like, that, when wrapped, has an increased light transmission, and the method of manufacture thereof.

BACKGROUND

The chemistry of making soap is well known to the art. Processes for the manufacture of light transmitting soap, including those designated as transparent, have also been known for a long time; the oldest product known at this time being the English soap "Pears Transparent" which was first offered for sale at least as long ago as 1789, or over two hundred years ago.

A continuum of light transmitting soap exists. By accepted definition, "transparent soap" includes any soap through which a person of normal vision can see 14 point type through a bar approximately 0.65 cm thick Wells, F. M., *Soap and Cosmetic Specialties,* 31(6–7) June–July 1955. This definition includes soaps having various colors and hues.

Since at least 1875, transparent soap containing a message or other object has been known to the art. Strunz, R. E. U.S. Pat. No. 6,624 reissued Aug. 31, 1875 is the oldest patented example known to applicant. Numerous other transparent soaps with interior messages or articles have been found to exist, including Villain, U.S. Pat. No. 1,827,549 issued Oct. 13, 1931, and Inui et al U.S. Pat. No. 4,504,433 issued Mar. 12, 1985.

These patents share similar disadvantages. They require a multi step manufacturing process where at least a portion of the soap bar has hardened before the balance of the bar is cast, and then requires the solid and molten portions of the bar to fuse. They also pay no attention to the perceived transparency of the packaged finished product.

Even O'Neill U.S. Pat. No. 3,926,828, issued Dec. 16, 1975 for a method of making soap bars having increased maintained transparency, ignores the transparency of the packaged finished product.

O'Neill briefly discusses, see Col. 5 line 42—Col. 6 line 2, factors that can adversely effect transparency of a bar of soap. However even O'Neill fails to consider what effects the packaging of the finished product may have upon the transparency of the finished, packaged, product.

To a far greater extent than discussed in Wells, F. M., *Soap and Cosmetic Specialties*, 31(6–7) June–July 1955, transparent products are apparently perceived to be desirable. Products from dish soaps to soda pop have employed clear formulations, many in transparent packages, to enhance their supposed appeal to the consumer. Similarly, there appears to have been little use of light transmitting soap, either alone or in a composite bar, for decorative purposes.

Also, unlike the famous floating IVORY® soap bar, which has a specific gravity of under 1.00, applicant is unaware of any transparent glycerine soap bar having a specific gravity of less than 1.00, Similarly, applicant is unaware of any transparent bar containing voids or air pockets within the bar which do not render the bar less transparent.

Prior to the filing of the parent application, such light transmission, or even transparency, has not been effectively employed with solid soap. First, there has been little manufacture of truly transparent soap, for which the accepted term appears to be "water clear". Second, little attention has been paid to the physics involved in transparently wrapping a light transmitting solid so that the light transmission of the finished product, in its transparent wrapping, may be observed. Third, absent such a clear wrapping, there has been little incentive to produce either simple or composite decorative light transmitting soap. Fourth, only after the filing of the parent application, have the impact of certain factors come to light.

This improved light transmission for packaged light transmitting soap cannot be accomplished simply by wrapping a solid bar of light transmitting or transparent soap in a clear plastic wrapper. While this method can be observed in the market place to work with clear liquids, the physical interfaces are different when a quasi solid soap bar is wrapped with flexible wrapping. The apparent, or observed light transmission of the soap is markedly diminished.

Further, such wrapping problems dramatically inhibit the use of light transmitting soap as a display piece. A soap bar intended for display could well contains objects such as artificial flowers or birds inside the bar of transparent soap, allowing such bars to serve as decorative objects. Alternatively, such a bar could contain a visual representation of an island in an ocean, with, for example, the name of the island superimposed over the island.

Even with the most transparent soap presently known to the art, and transparent wrap, the perceived transparency of the soap, as the individually wrapped soap, that is wrapped soap where the wrap is not in contact with molten soap, is displayed for sale, is substantially impaired. Applicant believes that this impaired transparency limits the utility, and the sales appeal, of such product.

As is also well known to the art, desired aroma emitting products, such as air fresheners, scent emitting paperweights, aroma therapy soaps, and the like, can, if desired, be manufactured in the same manner, and from similar ingredients as soaps, and have had even less attention directed towards their packaging. The visual transparency of such composite product, what ever its name, after wrapping, is substantially degraded.

These problems, though addressed, in part, in the parent application, have not been totally resolved prior to the filing of the subject application. Further, such a bar having a greater degree of durability would be highly desirable.

Applicant perceives that these concerns leaves a void which needs to be filled. It is towards filling this void that the subject invention is directed.

BRIEF SUMMARY OF THE INVENTION

The subject invention comprises a wrapped light transmitting bar having an increased degree of observed light transmission. In a sentence, the invention comprises having a molten transparent soap or soap like substance come into contact with a transparent wrapping material, and solidify while in contact with the transparent wrapper, thereby creating a wrapped transparent solid having enhanced clarity.

The finished good may be a bar of soap, a aroma emitting paper weight, an air freshener, or other object manufactured from transparent soap like feed stock. For simplicity, the material will be referred to as soap. The molten liquid soap is well known to the art, and is particularly well suited to having an object, or objects placed there within during the casting process and thereby having the objects fixed within the bar when the molten soap has solidified.

Subsequent to the filing of the parent application an article of manufacture having controlled voids within the soap has been created. These voids may be created by the placing of wires or the like in the volume into which molten soap is poured, and then removing such wires during the cooling process. Hollow members may be used in place of wires. Dyes may be placed on such wires or members, in combination with a soap coating or solution to lend color to the voids when remain after the wires have been removed. If desired, these voids can create interesting visual effects, and even, a product which has a specific density of less than 1.00.

Additionally, improved methods of manufacturing packaged bars having an improved perceived clarity have been developed. These methods involve using stronger transparent wrapping, and placing an amount of downward force on the wrapping which is greater than that produced through gravity. Typically such force would be created by placing pressure on the top of the bar, or using a partial vacuum to pull downwardly on the wrapping which holds, contains, and is in contact with the molten soap placed therein.

In brief, an embodiment of the process is as follows: A typical highest quality, most transparent, glycerine soap mixture is heated, or reheated after an intermediate period of drying, to normal pouring temperature. A piece of clear stretchable plastic wrap is prepared to receive the heated molten soap, typically by being placed in the bottom of the mold and then tensioned by the mold, allowing sufficient excess wrap to be retained so as to completely wrap the cast bar after cooling. A heavier, more durable piece of plastic wrap may be used, if desired, if the amount of downward force applied to the plastic wrap is increased from that created by the operation of the normal gravitational pull of the Earth.

An alternative embodiment of the invention is to take a bar of such material, wrap it with clear wrapping when cool, and reheat the wrapped material to a temperature above the melting temperature of the soap, so that the outer surfaces of the bar return to the molten state. The level and duration of heating can range from approximately 70 to approximately 95 degrees Celsius, and from approximately 2 to approximately 60 seconds. Care must be taken to avoid an over melting of the bar. This bar, and the wrap can then cool together and form a similar transparent interface and have a similar appearance to that of the initially disclosed invention in the parent application.

If desired, an object, such as an artificial flower may placed upon the portion of the wrap prepared to receive the molten soap, face down, before pouring is commenced. Means of leaving a void in the soap bar may also be employed, either before, pouring, after pouring, or both. After such an object, if desired, is placed in the desired location on the wrap, the liquid soap is poured up to the desired fill line, thereby coming into direct contact with the wrap. The voids may attain a variety of desired appearances, and may even reduce the specific gravity of the wrapped bar below 1.00.

Preferably, the temperature of the molten soap is maintained within a close tolerance while a spigot, or another suitable attachment is used to do the pouring. A variety of feed stocks, and a variety of dyed or pigmented soaps may also be used. In a particular embodiment, a multi step pour into the stretchable plastic wrap may also be used.

Up to approximately 90% of the total surface area of the poured molten soap could be in contact with the wrap at the conclusion of pouring. A typical pour temperature would be approximately 90 degrees Celsius. Alcohol mist is then sprayed on the top uncovered portion of the soap, if needed immediately after pouring is completed, to pop foam.

After pouring, while the soap is solidifying, the cooling soap needs to be maintained in a vibration free environment. The combination of heat, gravity, any added positive or negative downward force, and the restorative force of the plastic wrap will cause the soap to form into a convex curved shape, having a variable, but controllable, radius of curvature.

Applicant has discovered that adding to, or subtracting from, the amount of downward force naturally applied by the interaction of mass of the soap and the usual acceleration due to gravity, approximately 980 $cm/s^2$ applied to the packaging material, either directly, or indirectly through the soap, effects changes in the shape of the soap bar, and changes the strength of packaging material which may be employed. If desired, increased, or decreased, downward force may be applied to the packaging material, to either effect the radius of curvature of the soap, permit the use of thicker or stronger plastic wrap, or both. An amount of vacuum approximating 15–20 inches (38–51 cm) of water, has been found to be particularly suitable. Pressure of a similar amount could also be applied to the top of the molten soap.

The soap containing mold is then typically removed from the mold base. The soap and plastic are then removed from the mold, without removing, or disturbing, that portion of plastic wrap in contact with the soap from its contact with the soap. If desired, the soap is then allowed to dry. After any desired drying, the soap is then wrapped with the remainder of the sheet of plastic wrap to which the soap has been connected since pouring. The remainder of the packaging process then proceeds in whatever conventional manner is most appropriate, or otherwise selected or desired.

This process may be employed to create diverse finished products from similar feed stocks. Such products could well include air fresheners, scent emitting paper weights, aroma therapy soaps, and the like.

Accordingly, a prime object of the subject invention is to provide, as an article of manufacture, a light transmitting bar wrapped in transparent flexible wrapping, thereby having an enhanced degree of light transmission when wrapped, when compared to present wrapping techniques as applied to transparent bars.

Another object of the subject invention is to provide a novel and unique transparent bar of soap having an object inside the bar of soap which is more visible than prior art objects similarly situated inside transparently packaged transparent soap cast and manufactured in accordance with the prior art.

A further object of the subject invention is to provide a novel process for the production of light transmitting soap bars wherein the soap bar is cast in contact with its transparent packaging material.

Still another object of the subject invention is to provide a novel process of manufacturing light transmitting soap bars having an artificial object inside the bar wherein the artificial object is placed on the transparent packaging material, the entire bar is cast in a single pouring, and the soap is cast while contained by its flexible transparent packaging material.

Yet another object of the subject invention is to provide a novel multi step process where various feed stocks are sequentially, and in reasonable time proximity, poured into a sheet of stretchable plastic wrap which will then wrap the poured bar after cooling.

A yet further object of the subject invention is to produce as an article of manufacture a transparent bar having both an object and controlled defined voids in the interior thereof.

Still another object is to create an improved process for manufacturing high transparency packaged transparent soap whereby the application of increased downward force on the clear wrapper of the soap allows the use of stronger, heavier, or both plastic packaging material.

These and still further objects as shall hereinafter appear are readily fulfilled by the present invention in a remarkably unexpected manner as will be readily discerned from the following detailed description of an exemplary embodiment thereof especially when read in conjunction with the accompanying drawings in which like parts bear like numerals throughout the several views.

BRIEF DESCRIPTION OF DRAWING

In the drawing:

FIG. 11 is a data chart demonstrating the increased perceived optical clarity obtained by the subject invention.

FIG. 12 is a simulated enlarged chart of symbols which could be used in conducting the Noble Perceived Optical Clarity Test.

DESCRIPTION OF PREFERRED EMBODIMENTS

The subject invention, described through out by the reference 10 comprises a process, and an article of manufacture 14, as will be more fully described below.

Figure 1:
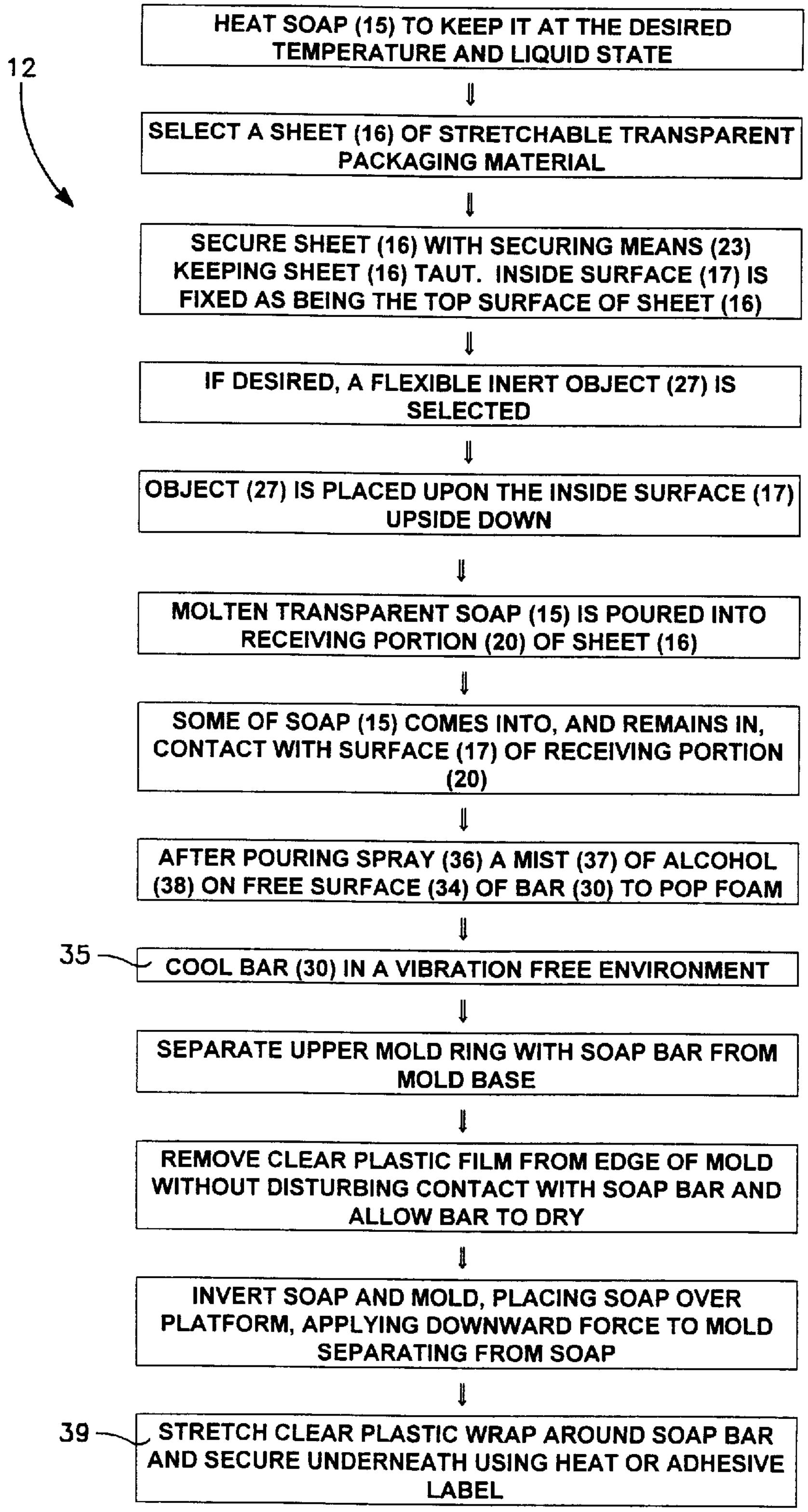
FIG. 1 is a flow diagram of a soap process embodying the subject invention.

Referring to FIG. 1, one practice of the process comprises taking light transmitting soap 15, in either a liquid or solid state, and applying sufficient heat to soap 15 to keep it at the desired temperature and liquid state. This desired temperature is well above the melting point of the soap 15, but below the ambient boiling point of water, 100 degrees C. at sea level, at which point damage occurs to the soap 15. A typical temperature might be 90 degrees C. Further, as defined herein, soap 15 includes transparent soap, as well as transparent synthetic detergent or other cleansing composition, or a similar composition which emits a desired or even pleasurable scent.

Concurrently with, or prior to, the heating described above, as shown in FIGS. 1–7 and 9, a sheet of transparent packaging material 16 must be selected, which has an inside surface 17 and an outside surface 18, which may be indistinguishable, for each bar 19 of soap 15 which it is desired to cast during a production run or period of time. This material 16 is preferably a transparent stretchable plastic wrap which has reasonable, though not absolute, resistance to temperatures up to at least 100 degrees C. For the basic embodiment of the process polyvinyl chloride (PVC) shrink wrap has been used. For the enhanced embodiment, described in FIG. 10 and shown in FIGS. 6–9, SARAN WRAP® brand polyvinylidene chloride (PVDC) film has been found to be particularly suitable. A polyethylene film may also be used if extreme temperatures are not employed, as shown in FIG. 1. Sheet 16 is comprised of receiving portion 20 and wrapping portion 21 whose functions will be more fully described below.

Figure 2:
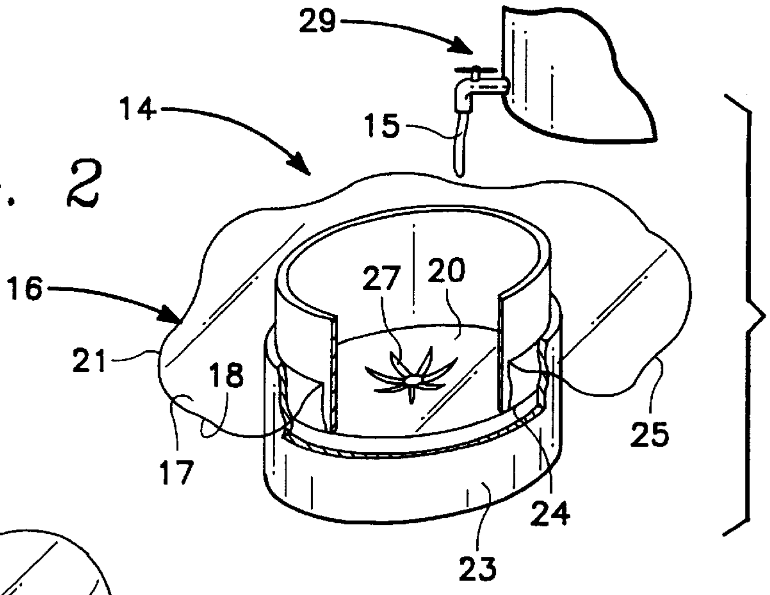
FIG. 2 is a drawing of a sheet of transparent packaging material, with a porous artificial flower inserted therein, just before pouring.
Figure 3:
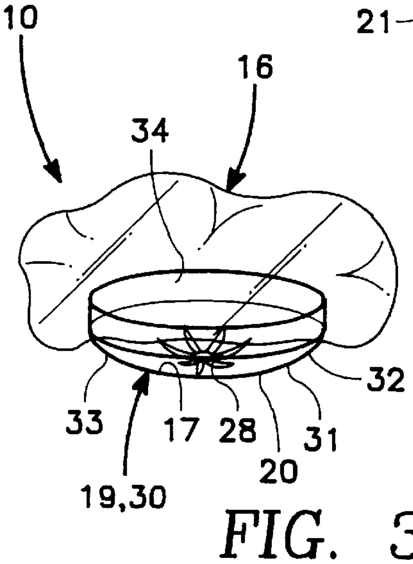
FIG. 3 is a drawing of a soap bar, immediately after cooling.
Figure 4:
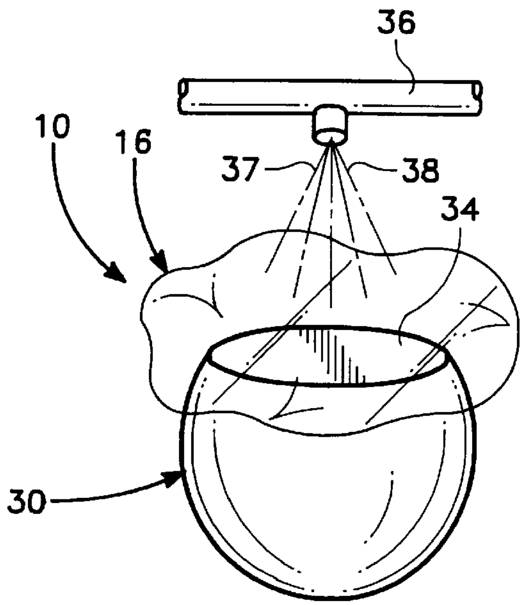
FIG. 4 is a drawing of a semi spherical soap bar after pouring.
Figure 5:
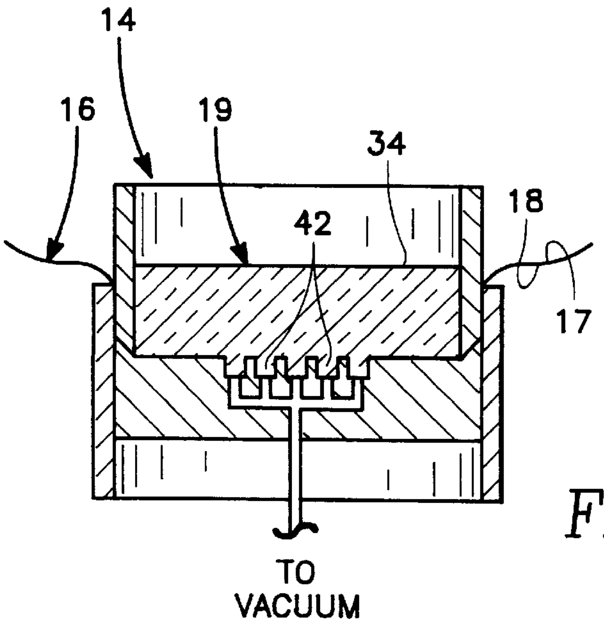
FIG. 5 is a drawing of an embossed transparent soap.

As shown in FIG. 2, sheet 16 is secured by securing means 23, which may have a bottom that is open, partially covered, or totally covered, so that all of receiving portion 20, and the proximate portion 24 of wrapping portion 21, both of which are located within securing means 23, are kept reasonably taut, while the remote portion 25 of wrapping portion 21, which is not within securing means 23, and is positioned so as to be available when needed, but to not interfere with process 12. Commonly, securing means 23 may comprise mold means which both secure sheet 16, fluid tight, and capable of being released without disturbing sheet 16. By securing sheet 16 within securing means 23, inside surface 17 is fixed as that surface being the top surface of portion 20.

Figure 6:
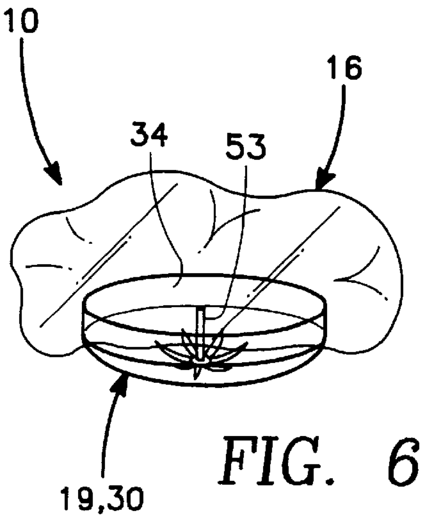
FIG. 6 shows a bar of soap having defined voids created in the interior of the soap.
Figure 7:
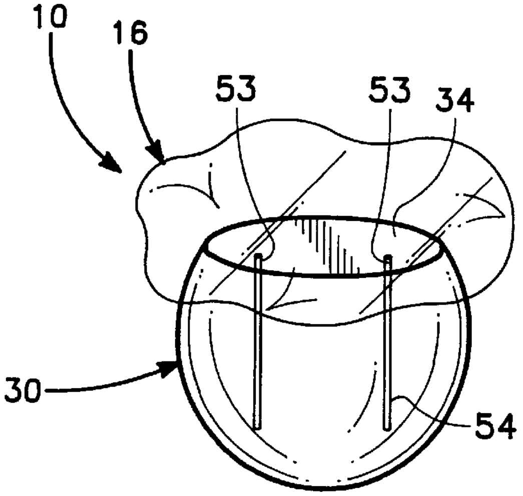
FIG. 7 shows the application of additional downward force to the packaging material.

If desired, an inert object 27, such as a silk flower, a plastic object, or even a solid object is selected. As shown in FIG. 6, a void crating object 27*a* may also be inserted. Object 27 has a side 28 which is intended to be visible at the conclusion of process 12. Object 27 is generally placed upon the inside surface 17 of receiving portion 20 of sheet 16, so that side 28 of object 27 is proximate to, or in contact with, surface 17 of receiving portion 20 prior to the commencement of pouring 29.

In other alternative variations of process 12 object 27 could be any coloring agent such as a pigment or dye, or other material having the proper physical properties. Additional objects 27*a* may also be inserted within the volume into which soap 15 is poured. These objects 27*a* could, if desired, could have a coloring agent placed thereupon, so that the coloring agent will remain after the objects 27*a* are removed. Objects 27*a* could be either solid, such as a pin, or a hollow tube.

The pouring 29 of molten soap 15 into receiving portion 20 of sheet 16 then commences. Pouring 29 continues until the desired amount of soap 15 is poured into receiving portion 20, and may be either discrete or continuous. This pouring 29 and the energy contained by the molten soap 15 inherently forces the air out of the volume occupied by molten soap 15. A typical amount of soap to be poured for a single bar is approximately 115 g., though any suitable quantity could be used.

As molten soap 15 is poured into portion 20, which serves as a mold for soap 15, some of soap 15 comes into, and remains in, contact with surface 17 of receiving portion 20, while soap 15 assumes the desired shape of soap bar 30. Molten soap from subsequent pours may or may not come into contact with surface 17. Soap bar 30 has an exterior surface 31, and an interior 32. Surface 31 is divided into contacted surface 33 which is in contact with surface 17 of portion 20, and free surface 34 which is not in contact with surface 17, of portion 20. Accordingly, surface 34 is exposed.

Upon the completion of pouring of light transmitting soap 15, prior to either additional pouring of additional soap or cooling 35, the next step is spraying 36 a mist 37 of alcohol 38, such as ethanol or other suitable short chain straight alcohol, on free surface 34 of such portion of bar 30 as has been poured. The purpose of mist 37 is to pop foam, if needed. However, this is important only relative to light transmitting soap 15, and not soap containing a pigment, as foam would impair the transmission of light through the light transmitting soap.

The cooling 35 of bar 30 is critical to process 12. Cooling 35 must take place in a manner that is substantially vibration free. Cooling 35 must also not be forced excessively, with bar 30 being allowed to cool, to the ambient temperature, preferably approximately 20 to 25 degrees C., in approximately 30 to 60 minutes, or longer.

Upon the completion of cooling 35, bar 30, and sheet 16 which is partially attached thereto, are removed from restraining means 23, while maintaining the preexisting contact between contacted 33 and surface 17 of portion 20. Drying may be allowed to occur, if desired.

Packaging 39 then occurs. The necessary areas of wrapping portion 21 are then placed into intimate surface contact with free area 34, so that as nearly as possible there is a smooth air and wrinkle free interface between portion 21 and area 34. The remainder of packaging 39 then takes place in a conventional manner. Upon the completion of packaging 39, the article of manufacture 14 has been produced.

Figure 8:
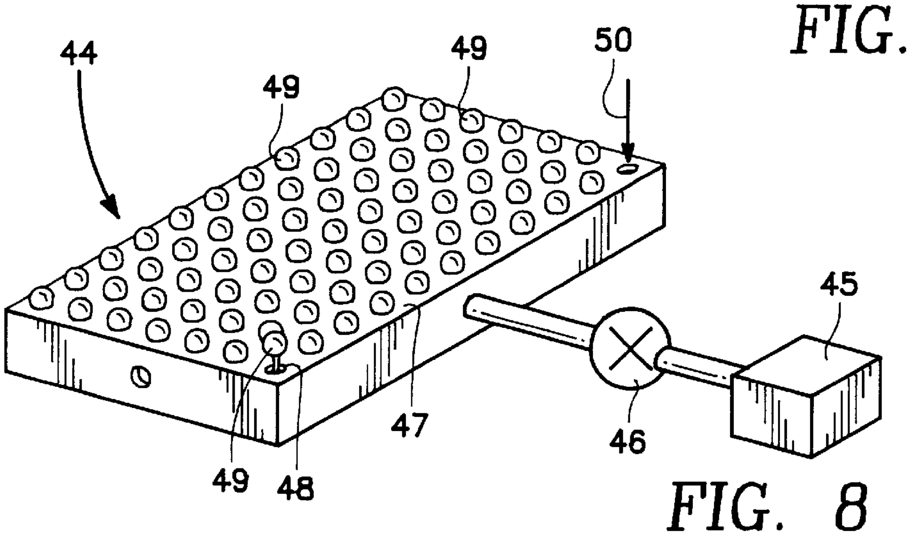
FIG. 8 shows a surface for applying downward force to cooling soap.
Figure 9:
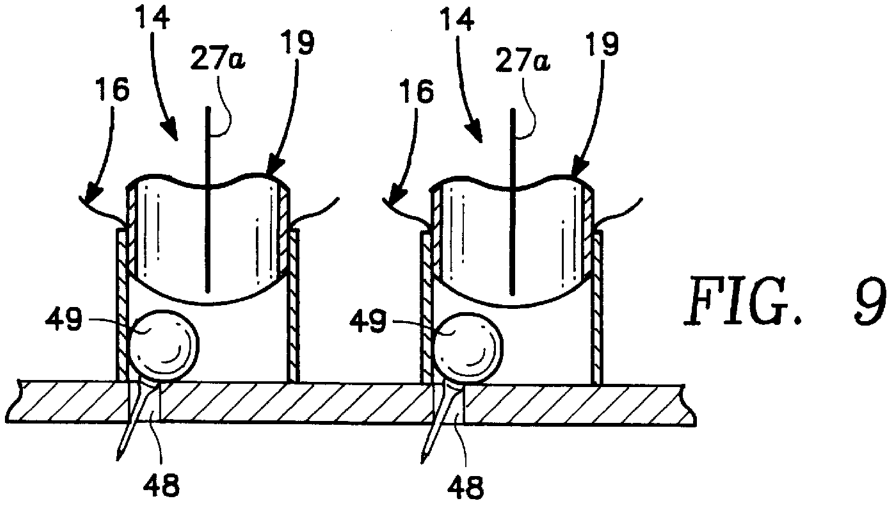
FIG. 9 is a detailed view of a mold having downward force applied thereto.
Figure 10:
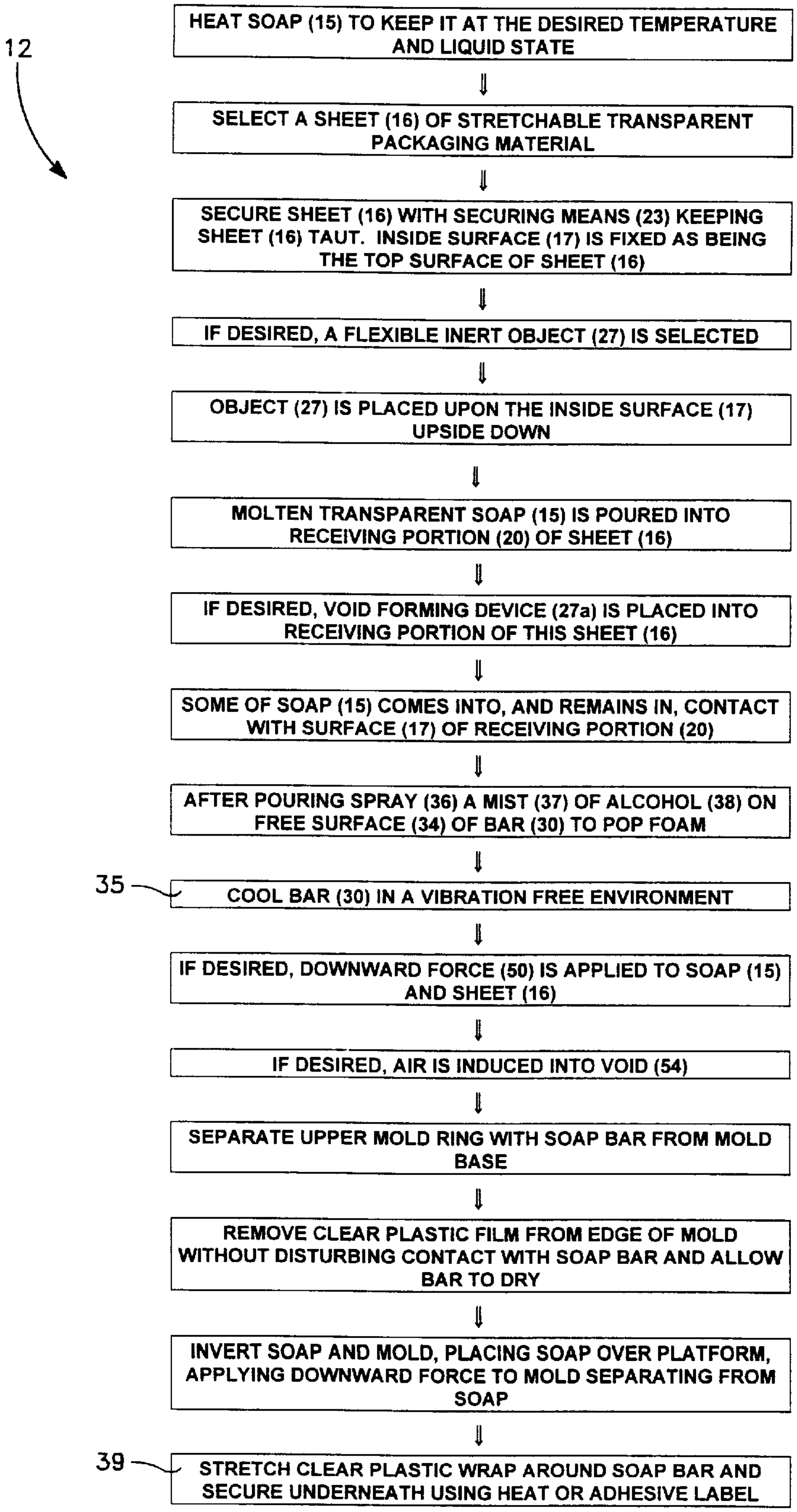
FIG. 10 is a flowchart of the process which may employ the creation of voids and/or added downward force

As shown in FIGS. 8–9, pressure differential means 44 was constructed comprising of pressure generating means 45, pressure adjusting means 46, surface 47 having holes 48 inserted therein of such a diameter so that individual valves 49 could be inserted therein. Means 44 is employed in the following manner.

The molds 20 were prepared by inserting a sheet 16 having an approximate thickness of 0.0015 cm and having temperature resistance to over 100 degrees C. inserted therein. SARAN WRAP® brand polyvinylidene chloride (PVDC) film has been found to be particularly suitable for this mode of carrying out the invention, as it has a higher degree of strength and is more resistant to moisture loss than plastic shrink wrap described above. Soap 15 is poured into sheet 16 in the manner previously described.

After pouring, the soap filled molds 20 are placed on a vibration free table which also serves as a pressure differential means 44, such as is shown in FIG. 8. After the molds are placed thereupon, force 50 is actuated, Such force should be actuated within about 20–30 minutes after pouring.

The procedure described above is employed with the exception that at some time during the cooling process the soap 15 contained and in contact with wrap 16 is subjected to downward force 50. The amount of force 50 may be varied from between approximately 0 to approximately 60 inches of water, (0–155 cm) of water as desired, depending upon the curvature desired, and the strength of the wrap 16 employed. A greater degree of force 50, for a given amount of soap 15, in a given mold, produces a smaller radius of curvature.

Force 50 may be applied to either the top of the soap 15 or the bottom of wrap 16. If force 50 is applied to the top of the soap 50 a positive force, such as a compressed gas is employed. On the other hand, if the force 50 is applied to the bottom of sheet 16, a partial vacuum may be utilized.

For use in conventionally shaped soaps produced soaps shaped by the subject invention, force 50 in the magnitude of from approximately 15 to approximately 20 inches (approximately 38 to 51 cm) of water appears to be most desirable with the combination of pour temperatures, weights of soap, and wrap employed, for the shape desired. This downward force 50 can be applied to a multiplicity of units, either in single or multiple chambered molds. As a vacuum, force 50 has been successfully employed and has been successfully employed in arrays of up to 11×7.

With or without the use of force 50, objects **27*a* can be inserted into the moltensoap 15 after pouring. By coordinating the objects 27*a* and the application of force 50, hollow air filled voids 53, having surfaces 54, in the soap 15 can be created in a variety of shapes, spaces, and locations. The voids 53 may be positioned in reasonable proximity to a portion of object 27, In particular voids 53 can be coordinated with surface 28 of object 27 to create a more lifelike appearance for object 27. If desired, pigments could be applied to some or all of surfaces 54 to create desired visual effects, such as stomata or pistols, employing in part a coating of such objects 27*a* with a soap containing solution (not shown). The metal wire 27*a* would retain sufficient liquid dye to leave the dye in the soap 15 on surfaces 54 after wires 27*a*** were removed during the cooling process.

Various alternatives to this method exist, and are feasible, so long as the essential step of placing moltensoap 15 into contact with the clear stretchable wrap 16 is maintained. One, and a preferred, manner of placing such soap 15 into contact with wrap 16 is through pouring the molten soap into the wrap 16 as previously described.

Another manner of placing molten soap in contact with such wrap 16, is through the heating of a bar 30 consisting of soap 15 surrounded by wrap 16. In any event, the tautness of wrap 16 needs to be maintained. To date such heating, in water, and presumably as well in another suitable liquid, has been successful in obtaining results substantially identical with those of pouring soap 15 into shrink wrap 16 without employing downward force 50.

The preferred results are obtained through the use of a heavier wrap 16, in conjunction with the use of downward force 50, which appears to aid in areas such as reducing moisture transfer, or abrasions, which are believed to be factors which have adversely affected the duration of transparency of bars 30. The use of the heavier wrap 16 definitely increases the perceived optical clarity of bars 30.

Compositions having coloring agents, such as dyes or pigments may be used. Vacuum embossing may also be used to create a three dimensional relief 42. Different soaps 15 may be poured into the plastic wrap 16, sequentially, in an interval ranging from reasonably close time proximity, as close as 20 to 30 minutes, to whatever time may be desired, to obtain a composite effect visible through light transmitting bar 30. Multiple soaps, and raised relief figures, can be combined if desired. Additionally, if pouring can be accomplished without creating bubbles, then, in that event, there is no foam to pop, and no need to spray an alcohol mist on the free exposed surface of the poured molten soap.

The measurement of the manner in which an object inside a bar of soap may be perceived is difficult. Applicant has just become aware of a method for measuring the transparency of a bar of soap invented by Joshi and described in U.S. Pat. No. 4,493,786 col . . . 14 lines 51–68 and col . . . 15 lines 1–9. However this method is inapplicable to the subject invention, because the measurement of clarity, to have any meaning, needs to be done through a wrapped bar, unlike the Joshi test.

What applicant believes that he has invented is a bar of soap, and a method of manufacture thereof, where an object inside the bar of soap can be perceived more clearly than was previously possible. For lack of an existing term, applicant describes this quality as perceived optical clarity. Applicant believes that this quality may be affected, for a given object within a bar of soap, by a variety of factors, including soap clarity, film clarity, soap color, interface clarity, bar shape, and others.

None of these characteristics of a wrapped bar of soap can be directly measured through non-destructive testing. Applicant believes that he has created a method of quantifying the compositor effect of the factors effecting the manner in which an object within the transparently wrapped transparent bar may be seen.

Applicant conducted tests to measure the perceived optical clarity of finished the original and enhanced methods. The test employed was to embed a chart reduced in size from that shown in FIG. 12, having the characteristics described in Table 2, in various bars of soap, without disturbing the naturally occurring interface between the transparent wrap and the transparent soap.

As stated above, the bars indicated were each viewed from a fixed distance of approximately 60 cm. The lighting was kept constant for each subject. Each subject was unaware which sample he or she was viewing. The amount of soap that the chart was viewed through was approximately 0.65 cm. The results of this test appear in FIG. 11, Separate tests had previously established that the perceived optical clarity of freshly wrapped and poured bars prepared using either shrink or improved wrap was substantially identical. This test demonstrated that the perceived optical clarity of the soap manufactured with the aid of downward force, which allowed the use of the stronger wrap, maintained substantially all of its clarity for at least a 6 month period.

The sizes of characters, not just alphanumeric symbols employed ran from 10 point down to 2 point, in "True Type" ARIAL as shown in Table 2 below:

TABLE 2

| Line Number | Size in points | Number of Characters in line |
|---|---|---|
| 1 | 2 | 13 |
| 2 | 3 | 10 |
| 3 | 5 | 9 |
| 4 | 6 | 7 |
| 5 | 8 | 6 |
| 6 | 10 | 5 |
| Total Number of characters | | 50 |

In a separate test, a substantially identical chart was embedded under approximately 3.6 cm of transparently wrapped poured in the wrap molded transparent soap was viewed under bright light at whatever distance was deemed best by the subject; 4 subjects were tested. All of the subjects correctly identified at least 49 of the 50 characters, with any incorrect items being found in line number 1, and at least 92% of the 2 pt. characters. No control was used for this test. The subjects were allowed to wear only their usual eyeglasses or contact lenses, if any.

Applicant submits that demonstrates an unusual level of perceived optical clarity of wrapped transparent soap, as the classic defining test for transparent soap is the ability to perceive 14 pt. characters through soap slightly less than 0.65 cm thick. In this test objects 7 times smaller was seen through more than 5.5 times as much soap. If meaningful, the difficulty product of this test would mathematically approximate 38.5.

In an aid towards the further understanding of the subject invention, and solely as being illustrative, and not in limitation thereof, applicant offers the following examples:

EXAMPLE 1

Procedure 1

A highly light transmitting composition which meets the definition for transparent soap was prepared from a well known formula, having the following approximate weight/weight percents:

| Ingredient | Weight/weight % |
|---|---|
| Coconut oil | 19.0 |
| Stearic Acid (triple pressed) | 10.0 |
| Castor Oil | 8.0 |
| NaOH aq (33% strength) | 21.2 |
| Table sugar (granulated cane) | 14.5 |
| $H_2O$ (deionized) | 16.0 |
| Propylene Glycol | 5.0 |
| Glycerin | 6.0 |
| Fragrance (if desired) | 0.3 |

The coconut oil, stearic acid, and castor oil were mixed and warmed together, forming a heated solution. The NaOH was warmed to approximately sixty degrees C., and then stirred into the heated solution.

The heat was then removed from the combined solution. The combined solution was then allowed to set in a covered container for approximately two hours, so that saponification could occur.

Sequentially, the glycerin and propylene glycol were individually stirred into the batch of transparent soap. Any insoluble matter was then removed from the batch.

The water was then heated to approximately sixty five degrees C. so that the sugar could be dissolved therein. The sugar solution was then slowly added to the batch. If necessary, the pH of the batch could be adjusted so as to minimize free alkali by the addition of coconut fatty acids.

The soap was transparent, but had an amber color. Applicant believes, but does not desire to be bound thereby, that the amber color was due to the presence of castor oil. The soap was molded into slabs, and allowed to dry for at least a month.

Procedure 2

A slab of soap made in accordance with procedure 1 was selected. Its color was unchanged. The slab was placed in a suitable vessel, and returned to a molten state, and held at the pouring temperature of approximately 90 degrees C. A selected fragrance oil was added to the molten soap.

A mold was prepared. A sheet of stretchable plastic was placed in the mold, and kept taught thereby. A suitable quantity, approximately 113.5 g. of scented liquid soap was poured into the plastic sheet, forming a contact between the soap and the plastic sheet. An ethanol solution was sprayed on the uncovered portion of the soap to pop foam.

The soap filled mold was kept in a vibration free environment and was allowed to cool for approximately 60 minutes. The combination of gravity, heat, and the physical properties of the wrap caused the soap bar surface in contact with the wrap to cool in a uniform lens like shape. No irregularities were visible through that portion of the wrap. The cooled transparent soap was removed from the mold without disturbing the contact between the soap and the wrap.

The free portion of the wrap was then used to surround the balance of the transparent bar. The appearance of the bar produce in accordance with Procedure 2 was compared with a bar of soap prepared in accordance with Procedure 1, allowed to cool and dry, and then be wrapped with transparent plastic wrap. The bar produced in accordance with Procedure 2 was visibly more transparent.

EXAMPLE 2

A slab of soap was prepared in accordance with Procedure 1. Procedure 2 was followed with the following addition. A fabric artificial small hibiscus flower head, purchased from Trade West, Inc., dba Nani Makana Distributors located in Honolulu, Hi., identified as part number 08270, was placed, face down on the taught portion of the plastic wrap, and the molten soap was poured there over. The balance of Procedure 2 was followed.

Because the flower was porous, some molten soap passed under the flower to come into contact with the plastic sheet. This contact was maintained during cooling. Upon the completion of cooling, a transparent soap bar, having an amber hue, and a highly visible artificial small hibiscus flower inside, was obtained. A comparison bar was produced using a conventional mold, and was wrapped in the same plastic wrapping. The bar produced in accordance with the modified Procedure 2 set forth above, had a greater apparent transparency; the flower was also much more visible.

EXAMPLE 3

Applicant then sought to obtain a soap base which would result in "water clear" soap, and other enhanced characteristics. Such a soap was obtained from Fullers'Soaps in Novato, Calif., and is commercially available, as well as being sold, unscented, at retail. This soap is produced in a proprietary process which is believed to be conventional in nature. The soap has a melting point of approximately 61.7 degrees C. and is believed to have the following general formulation identified as Composition 1:

| | weight/weight % | |
|---|---|---|
| Ingredients | min. | max. |
| Glycerin | 15 | 25 |
| Sodium Laurel Ether Sulfate | 15 | 25 |
| Coconut Oil | 8 | 20 |
| Safflower Oil | 8 | 20 |
| Sorbitol | 0 | 8 |
| Stearic Acid | 5 | 15 |
| Sodium Hydroxide | 3 | 8 |
| Water | 15 | 25 |

Larger bars of bulk water clear soap tends to have a frosty appearance due to the irregular dried surface which tends to occur during the bulk molding process. A desired amount of dried water clear soap, approximately 2070 g. was weighed out and melted. To prevent damage from overheating, the soap was melted in a double boiler type kettle. While the soap was being melted, the molds required for the entire batch of soap, in this case eighteen molds, were prepared in accordance with the procedure set forth in Example 2. After the soap had attained a molten state, and was stabilized at pouring temperature, the scent which corresponds with the artificial flower inserted is mixed into the molten soap.

The balance of the procedure set forth in Example 2, with the obvious substitution that the molten soap was identified as Composition 1, was followed. The resulting soap bars had a glass like appearance. The flower inside the soap bar was extremely visible.

EXAMPLE 4

A solid prepared in accordance composition 1 was melted. A raised relief piece, having holes there within to allow the creation of a partial vacuum was inserted inside the securing means prior to the placement of the sheet of plastic wrap therein. Air was removed from the piece so as to bring the wrap taught. The balance of procedure 2 was followed, with the additional step of maintaining the pressure differential throughout the cooling process.

The result was a highly transparent soap bar accurately expressing the relief of the raised relief piece. The plastic wrap remained in contact with the bottom of the soap even though the shape had a significant contour.

EXAMPLE 5

A solid prepared in accordance with composition 1 was melted, and divided into three portions. The first portion was heated to approximately 90 degrees C. The second portion was heated to approximately eighty degrees C. and had green Mearle Soapearl pigment dissolved therein. The third portion was heated to approximately 85 degrees C. and had blue Merle Soapearl pigment dissolved therein, A mold was prepared in the manner described in Procedure 2. A three dimensional representation of the island of Maui, Hi. was submerged into the mold to a depth with 0.3–0.4 cm of the flexible clear wrap which functioned as the mold bottom.

Approximately 50 g of the first portion of melted soap was poured into the mold at a temperature of approximately ninety degrees C., so that the level of the poured molten soap was approximately equal to the base of the artificial island. An ethanol mist was sprayed on the soap to pop foam This poured soap was allowed to cool for 25 minutes, which appeared to closely approximate the minimum time for the majority of the poured soap to solidify.

The artificial Island of Maui was then removed from the cooled soap, leaving an island shaped depression. Immediately thereafter, approximately 18 g. of the second portion of soap was poured, which was enough to just fill the island shaped depression. After approximately ninety seconds this soap had formed a solid skin.

Immediately approximately 45 g of the third portion was poured into the mold, thereby comprising the entire soap bar. The soap bar required at least another fifteen minutes to cool. The manner of packaging set forth in Procedure 2 was then followed.

Upon packaging, the soap bar was inspected. The blue portion closely resembled the ocean, while the pearlescent green was a little off in color, but still had a visually pleasing effect. The transparent portion of the bar had the same type of water clear appearance observed above.

EXAMPLE 6

The procedure set forth in Example 5 would be followed with the following variations. The pouring of the soap went extremely well in this case so that there would be no bubbles to pop and no need to spray an alcohol mist to pop foam. The first portion of soap would be allowed to dry for approximately one day. The second and third mixtures would therefore be able to be poured at slightly higher temperatures, though not to exceed ninety degrees C. The balance of the procedure set forth in Example 5 would be followed. The appearance of the soap bars produced pursuant to Example 5 and Example 6 would be indistinguishable.

EXAMPLE 7

Molten soap is prepared in accordance with one or more of the procedures above. Molds were prepared by placing 60 gauge plastic film approximately 0.015 cm in thickness between the mold pieces. In this embodiment of the invention the bottom edges of the mold base rings must be finished so that a close contact between the mold base and the flat table surface can be maintained. The plastic film was barely drawn taught. Artificial flower blossoms were placed face down onto the plastic film. To receive the molds a table was prepared. This table was comprised of a hollow chamber approximately 15 cm deep by approximately 95 cm by 120 cm. The upper surface of this table comprised a formica surface into which an array of 77 holes were drilled. The array was 7 by 11. The approximate diameter of the holes were 1.6 cm. Previously standard golf tees had been permanently attached to standard ping pong balls. One of these golf tees was placed in each hole. These golf tees served to correctly position the ping pong balls attached thereto which functioned as valves.

Vacuum attachments and slide valves were installed on the table. The vacuum was actuated. The valves were adjusted so that a vacuum level of 20" of water was maintained.

Immediately thereafter soap was poured in the manner described above. After the soap was poured into the mold and treated in the manner described herein the soap containing mold was slid laterally upon the table surface until the ping pong valve was pushed up and out of the hole it had covered. The golf tee locked the ball in place, preventing the ball from being pushed so far that vacuum would leak from around the edge of the mold based ring.

Additional molds were placed upon the table. The vacuum level was adjusted to maintain the desired pressure differential. As each filled mold was positioned and engaged the effect of the vacuum force was visible. After the table was filled with molds they were allowed to stand, in the vacuum, until all the soap had cooled and solidified. This cooling time was approximately one hour.

After solidification of the soap, the finished soap bars were removed from the mold and their wrappers attached over the entire face surface in the manner described above. The resulting bars had a high degree of uniformity and transparency which resulted in a bar that was visibly superior to those produced by other embodiments of the invention.

EXAMPLE 8

The general procedure employed in example 7 was followed with the following variations:

The filled molds were staged after pouring on a flat surface and cooled for approximately 20–25 minutes. This results in the soap being partially frozen. Just prior to initiation of vacuum a thin wire is poked into the top center of the filled mold.

This hole created a channel for air to enter into the uppercenter area of the soap and partially displaces the soap that shifts downward upon the application of vacuum drawing air into the area above the object suspended inside and against the ultimate soap face of the bar.

The best method known to the inventor involves using a small diameter hollow metal utensil which would be kept heated to approximately 95 degrees Celsius. Ideally the vacuum is subjected gradually over a period of 2–5 seconds. This method results in a different shape of the soap without adversely impacting the clarity or smoothness. The amount of air entrapped is adjustable.

The trapped air can be used for a variety of aesthetic purposes. If a minimal amount of air is trapped the visual affect of the artificial object is enhanced. If more air is entrapped visually pleasing effects even bubbles can be created. Further, by controlling the time in which the vacuum and hole are affected the positioning of the induced internal cavity can be somewhat controlled ensuring that, if desired, the cavity would remain behind the object molded in the soap bar when viewed from the face.

EXAMPLE 9

Transparent glycerin soap was obtained. This soap was wrapped in shrinkable plastic film in the conventional manner. The wrapped soap was heated in accordance with Table 1 below.

| Mass (g) | Degree C. | Time (s) | Wrap Used |
|---|---|---|---|
| 113.5 | 72 | 60 | shrink |
| 113.5 | 80 | 30 | shrink |
| 113.5 | 95 | 2 | shrink |

This heating was sufficient to place the outer portions of the wrapped soap bar back into the molten state. The heated soap was then allowed to cool to room temperature so that an interface between the plastic wrap and the soap in the manner of this subject invention was created. The cooled reheated soap had a substantially greater degree of perceived optical clarity than the conventionally wrapped transparent soap, that is soap not produced by having molten soap poured into plastic wrap, which had not been reheated. The appearance of the soap so treated closely approximated that of the subject invention where molten soap was poured into shrink wrap without the assistance of added downward force.

EXAMPLE 10

Several bars of conventionally produced transparent soap, substantially identical, except for the wrapping material used, to those treated in Example 9 above were obtained. These bars were heated by means of heated air. Such heating was attempted by means of both an oven and a hair driver. The results were uniformly unsatisfactory. However, no attempt was made to heat prewrapped bars at an ambient temperature range of from approximately 70 to approximately 95 degrees Celsius using the shrink wrap employed in the preferred embodiment of the parent application.

Applicant believes, but does not desire to be bound thereby, that the heat transfer properties of using heated air are insufficiently rapid to heat the bar satisfactorily. In such a case, the bar becomes distorted before the desired softening can take place to establish an air free contact between the wrap and the molten soap. Applicant believes that the success of this alternative depends on heating the film, are creating only a thin level of molten soap, without interfering with the structural integrity of the bar as a whole.

From the foregoing, it is readily apparent that a transparently packaged light transmitting bar and methods of manufacture thereof have been described and illustrated which fulfills all of the afforestated objectives in a remarkably unexpected fashion. It is of course understood that such modifications, adaptations, and alterations as may readily occur to the artisan confronted with this disclosure are intended within the spirit of the present invention which is limited solely by the scope of the claims appended hereto.

Accordingly the following is claimed:

1. A process of manufacturing transparently wrapped light transmitting bars from glycerine soap comprising the steps of:

A. creating molten transparent soap;

B. providing a sheet of taut transparent wrap, said sheet having a receiving portion;

C. pouring said molten soap into said receiving portion;

D. cooling said soap while maintaining the tautness of said sheet and maintaining said contact between said soap and said taut sheet; and, E. repeating step C at least once wherein an indentation formed in the soap poured in a previous pour comprises all or part of a receptacle for soap poured in a subsequent pour.

2. A process according to claim 1 with the added step of placing, face down, an object on said receiving portion of said taut sheet before pouring said molten soap into said receiving portion of said sheet, and over said object.

3. A process according to claim 2 wherein said object is a flexible, porous object.

4. A process according to claim 1 having the additional steps of applying a downward force to said soap and said sheet during the cooling of said bar.

5. A process according to claim 1 wherein said molten soap consists of a plurality of different compositions individually poured through a plurality of outlets into a single receiving portion at substantially the same time in a single pour.

6. A process according to claim 1 wherein said one or more of said compositions of molten soap contain different dyes or pigments.

7. A process according to claim 1 wherein said one or more of said compositions contain different dyes or pigments.

8. A transparently wrapped bar having a mean perceived optical clarity index of at least 0.90, at the completion of the bar manufacturing process, when said index is measured on the Noble Perceived Optical Clarity Test, said process comprising: creating molten transparent soap, selecting a sheet of transparent wrap large enough to completely wrap the solidified soap bar, securing said sheet so that a receiving portion thereof is positioned to receive said molten soap and a wrapping portion thereof is positioned to wrap said soap bar after cooling, inserting a hollow object into said receiving portion, pouring said molten soap into said receiving portion of said sheet thereby establishing a contact between said soap and said receiving portion of said sheet, determining if light transmission inhibiting foam exists, eliminating such foam, if present, by spraying said poured molten soap with an alcohol mist to pop any such foam, cooling said soap bar while maintaining said contact between said soap and said receiving portion of said sheet, forcing gas into said soap thereby creating a void, repairing the integrity of said soap while retaining said gas in said soap, and completing the wrapping of said bar with said wrapping portion of sheet while maintaining said contact.

9. A bar according to claim 8 wherein said mean index is at least 0.94.

10. A bar according to claim 8 wherein said mean index, at least 6 months after manufacture, is at least 0.34.

11. A bar according to claim 8 wherein said index, at least 6 months after manufacture, is at least 0.94.

12. A bar according to claim 8 which has gas trapped within said bar in an intentionally created void.

13. A bar according to claim 12 which has a specific gravity of less than 1.00.

14. A bar according to claim 12 wherein a coloring agent may be present on the surface of a portion of said void.

15. A bar according to claim 8 which has an object inside said bar.

16. A bar according to claim 8 wherein a coloring agent may be present on the surface of a portion of said void.

17. A bar according to claim 8 which has an object inside said bar.

18. A bar according to claim 16 which has an object inside said bar.

19. A process for manufacturing transparently wrapped light transmitting bars from glycerine soap comprising the following steps:

A. Providing a sheet of taut transparent wrap, said sheet having a receiving portion;

B. Moving a plurality of different soap compositions individually through respective outlets into said receiving portion at substantially the same time;

C. Cooling said soap compositions while maintaining the tautness of said sheet and maintaining contact between said soap compositions and said taut sheet.

20. The process of claim 19 including the step of applying a downward force to said soap compositions during step C.

21. A process according to 19 wherein said one or more of said compositions contain different dyes or pigments.

22. A transparently wrapped bar having a mean perceived optical clarity index of at least 0.90, at the completion of the bar manufacturing process, when said index is measured on the Noble Perceived Optical Clarity Test, wherein said bar has gas trapped within an intentionally created void, said void having a coloring agent on the surface of at least a portion of said void.

* * * * *